United States Patent [19]

Prahl

[11] 4,366,583
[45] Jan. 4, 1983

[54] BREAST PROSTHESIS

[75] Inventor: Gertraud Prahl, Rullstorf, Fed. Rep. of Germany

[73] Assignee: IPOS Gesellschaft fur integrierte Prothesen-Entwicklung und orthopadietechnischen Service mbH & Co. KG, Lunenburg, Fed. Rep. of Germany

[21] Appl. No.: 183,891

[22] Filed: Sep. 4, 1980

[30] Foreign Application Priority Data

Sep. 20, 1979 [DE] Fed. Rep. of Germany ....... 2938019

[51] Int. Cl.³ ........................... A61F 1/00; A41C 3/10
[52] U.S. Cl. ........................................................ 3/36
[58] Field of Search ................... 3/36; 128/478–481, 128/462; 2/267

[56] References Cited

U.S. PATENT DOCUMENTS

| | | | |
|---|---|---|---|
| 401,028 | 4/1889 | Greene | 3/36 UX |
| 4,019,209 | 4/1977 | Spence | 3/36 |
| 4,172,298 | 10/1979 | Rechenberg | 3/36 |
| 4,184,214 | 1/1980 | Schaper et al. | 3/36 |
| 4,258,442 | 3/1981 | Eberl | 3/36 |

FOREIGN PATENT DOCUMENTS 5035 1/1957 Fed. Rep. of Germany ............ 3/36

*Primary Examiner*—Ronald L. Frinks
*Attorney, Agent, or Firm*—Beveridge, DeGrandi & Kline

[57] ABSTRACT

A breast prosthesis made from an elastic plastic material provided with a hollow body-like shaped breast part corresponding to the natural breast and a contact surfaced adapted to the human body shape having an opening connecting the inner space of the shaped breast part. The inner space of the shaped breast part is widened in dome-like manner as from the opening and has at least two vertical reinforcing or rolling ribs in the inner cavity area which are supported in such a way that they roll downwards on inverting-over the breast prosthesis. This leads to a constant strength distribution over the entire prosthesis periphery when the breast prosthesis is worn, corresponding to the natural breast, while simultaneously maintaining the elastic properties of the latter.

10 Claims, 1 Drawing Figure

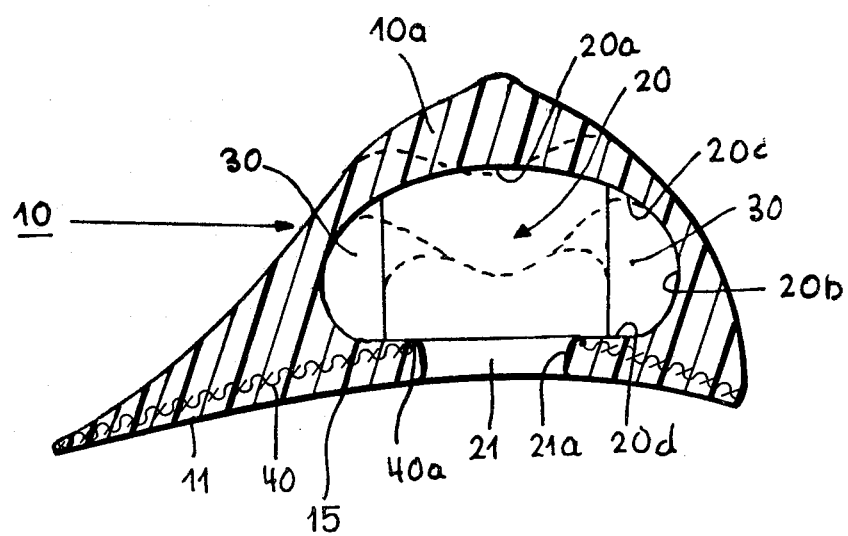

BREAST PROSTHESIS

BACKGROUND OF THE INVENTION

The invention relates to a breast prosthesis made from an elastic plastic material having a hollow body-like shaped breast part corresponding to the natural breast and with a contact surface adapted to the human body form having an opening connecting the inner space of the shaped breast part.

The tendency towards breast amputations is increasing, the amputation generally being a consequence of malignant tumours. As a function of the tumour size amputation leads to varyingly large scars and often to poorly covered body surfaces. The scars left behind by amputations are extremely sensitive to pressure edges and chafing points. In addition, breast amputation disturbs the symmetrical weight distribution on the vertical column, so that the following requirements are made on a breast prosthesis. The prosthesis must be adapted to the human body and must form a substantially closed contact surface on the body support side. The weight of the breast prosthesis must be selected in such a way that as far as possible it corresponds to the weight of the usually complete natural breast on the other side. In particular changes to the shoulder girdle and vertebral column must be avoided. The breast prosthesis volume must be such that it comes very close in its oscillation behaviour to that of the natural breast. The surface of such breast prostheses must be made from physiologically unobjectionable material because there are often scars with open points.

A breast prosthesis is known which is made from a flexible, one-part, air-free cup-shaped body which simulates the breast shape (German Utility Model No. 76 03 424). In this known breast prosthesis said body is made from addtition-crosslinked two-component silicone rubber, whose top and bottom surfaces are in each case covered by a plastic foil welded together along the edge of the cup-shaped body. The use of a breast prosthesis body made from addition-crosslinked two-component silicone rubber is intended to ensure that even when the wearer is moving the prosthesis will have the natural appearance, mobility and softness of the healthy breast, is easy to apply and pleasant to wear. Such prostheses having a cavity in the contact side area are cup-shaped, but do not fulfill the essential requirements made on a breast prosthesis. In particular the problems of the contact surface are inadequately solved and vertical oscillation balances, such as are of particular importance with larger breast shapes, are not attained.

In addition, a breast prosthesis with a flexible, one-part, air-free hollow body filled with a liquid and simulating the breast shape is known, being constructed as a double-walled cup simulating the outer shape of the breast (U.S. Pat. No. 2,543,499). Such air-free, liquid-filled, bag-like structures generally have a higher weight than the normal breast and have not gained acceptance because they are unnatural due to their hanging appearance. A further disadvantage of a liquid-filled prosthesis is that the fillers migrate and can flow out if the surrounding casing is damaged.

Another known breast prosthesis comprises either a body made from elastic, foam-like material or a hollow body made from light-weight, finely porous material having a filling of elastic and foam-like material (U.S. Pat. No. 2,851,692). Cylindrical cavities are provided within the breast prosthesis body which are provided with movable weights. Such prostheses are however so nondeformable that they cannot have the appearance of a natural breast.

In addition, breast prostheses made from a shaped foam body are known (German Pat. No. 13 03 139). This shaped foam body which has flat areas is surrounded by a cup-shaped, double-walled hollow plastic body which is spaced therefrom and is only connected to the foam body along its edge and is filled with a liquid. However, this breast prosthesis also has the disadvantage inherent in all liquid-filled breast prostheses. Furthermore, the construction of this known breast prosthesis is complicated and is unable to meet all the requirements made regarding a natural appearance.

A breast prosthesis comprising an approximately hollow cone-shaped member made from an elastic material, whose adhesion to the skin acts against undesired displacements of the prosthesis is contructed in such a way that the prosthesis is reinforced by internally fitted horizontally directed webs which are preferably made in one piece with the prosthesis (German Utility Model No. 17 39 612).

In addition, a breast prosthesis made from soft elastic, porous, adhesive, skin-coloured plastic, such as e.g. hardener-crosslinked, soft silicone rubber produced by shaped casting is known for placing or incorporating into a brassiere. It comprises a protruding, hollow central part, whose convex outer surface has the shape of a female breast with nipple and areola and, whilst maintaining the desired prosthesis wall thickness, its concave inner surface is curved in breast-like manner and centrally with respect to the nipple has a through-bore. Thin flexible edge branches surround the central part, whereof the shoulder-side edge branch is extended to form an extension, whose length and width are such that it is able to cover the axillary gland when the prosthesis is fitted. Thus, a breast prosthesis is allegedly obtained whose appearance and elastic properties largely correspond to those of the natural breast, which does not harm the skin and adheres firmly to the latter. In addition, it does not slip, is easy to wear, fits into standard brassiere sizes and can also be inexpensively mass-produced (German Utility Model No. 76 31 795).

Another known breast prosthesis which gives the wearer the feeling of weight balance and which can easily be compressed without the escaping air causing noises is constructed in such a way that horizontally directed reinforcing ribs and/or supports are provided on the concave inner surface of the shaped breast part and, for example, run radially from the outer periphery of the prosthesis towards the centre and in a preferred embodiment end before the centre (German Utility Model No. 78 13 097).

SUMMARY OF THE INVENTION

The problem of the invention is to provide a breast prosthesis which not only fulfills the basic requirements made hereinbefore on breast prostheses, but which also permits a constant strength distribution over the entire prosthesis periphery when the latter is worn corresponding to the natural breast whilst simultaneously maintaining the elastic properties, so that the prosthesis behaves in the same way as the natural breast.

According to the invention this problem is solved by a breast prosthesis of the aforementioned type in which the hollow space of the shaped breast part is constructed in dome-like widening manner as from the opening in the contact surface and has at least two approximately vertical reinforcing ribs or rollers in the internal peripheral area of the hollow space or cavity supported in the upper and lower areas of the latter in such a way that they roll downwards on inverting-over the breast prosthesis.

This breast prosthesis provides a shaped breast part which, when worn under the clothing can in no way be differentiated from the natural breast and therefore gives the wearer maximum wearing comfort, which can in particular be attributed to the constant strength distribution over the entire prosthesis periphery. The complete elasticity of the natural breast is maintained with the breast prosthesis. Due to the dome-like configuration of the internal cavity of the shaped breast part in conjunction with the reinforcing ribs arranged vertically in the wall side of the cavity a very good resilience is possible, accompanied by a good ventilation of the internal cavity and the latter can also be provided with additional ventilating openings. It is important in the case of the present rib structure that the reinforcing ribs roll downwards on inverting-over the breast prosthesis. This obviates tensions in the rib and eliminates crack formation, which occurs with the known ribs.

The problem of the invention is also solved by a breast prosthesis wherein the internal cavity of the shaped breast part widens in dome-like manner from the opening in the contact surface and has at least two approximately vertical reinforcing ribs located in the inner peripheral area of the cavity and which are supported in both the upper and lower cavity areas, wherein said ribs roll downwards when inverting-over the breast prosthesis and wherein a textile insert or layer is provided in the contact surface area of the shaped breast part covered on the contact surface side by a plastic layer, whose free edge region located in the vicinity of the opening is integrated into the plastic material of the shaped breast part. The textile layer runs in an inclined manner from the outer edge to the inner edge and towards the cavity a portion thereof is drawn into the plastic layer, whilst on the outside there is superficial engagement.

As a result of such a construction the textile insert, made from the plastic material known under the trade name Nylon, prevents tearing of the breast prosthesis, which only has a limited mechanical strength due to the use of very soft silicone rubber. The textile layer is consequently anchored in the breast prosthesis material. All textile coverings absorb moisture when the breast prostheses are cleaned with or in water. To reduce moisture absorption to a minimum the textile covering is not positioned on the outer surface of the breast prosthesis. The open textile face is here only the cross-section of the individual fibres of the textile insert. This further development of the breast prosthesis with a textile insert provides the advantage that moisture absorption is prevented, because breast prostheses require frequent washing.

DESCRIPTION OF THE DRAWING AND PREFERRED EMBODIMENTS

The drawing is a vertical section through a shaped breast part according to the invention.

The breast prosthesis comprises a shaped breast part 10 made from a homogeneous elastic plastic material. This shaped part 10 has an internal cavity 20, whose cross-section corresponds to that of a dome 20a. This internal cavity 20 passes into a smaller diameter opening 21 which issues into the contact surface 15 of shaped breast part 10.

The retracted transition between opening 21 and the dome-like internal cavity 20 is indicated as an inner peripheral area 20b. The peripheral edge of the portion of the shaped breast part 10 bounding opening 21 is designated by 21a.

The curved shaped breast part 10a is supported by at least two reinforcing or rolling ribs 30 shaped into the internal cavity 20 and supported at one end on the upper cavity area 20c and at the other end on the lower cavity area 20d of cavity 20. Advantageously three spaced reinforcing ribs 30 are provided in internal cavity 20. To increase the elasticity of the shaped breast part 10 the reinforcing ribs 30 do not extend into the vicinity of the peripheral edge 21a of opening 21 and instead terminate before said edge 21a, as indicated in the drawing.

The reinforcing or rolling ribs 30 roll downwards when the breast prosthesis is being inverted-over. This prevents stresses in the rib. This over-inversion process is shown by dotted lines in the drawing.

To prevent moisture absorption a textile insert 40, for example made from a nylon fabric or the like is embedded in the plastic material of the shaped breast part 10 in the vicinity of the contact surface 15 thereof. This textile insert 40 can be embedded in such a way that on the contact surface side insert 40 is covered with a layer 11 of plastic material, which is the same as that from which the shaped breast part 10 is made. The all-round edge 40a of the textile insert 40 is integrated into the plastic material in the rim area of opening 21 in such a way that in the vicinity of opening 21 textile insert 40 engages in the latter with a small edge portion. This leads to a high strength of textile insert 40 in the plastic material of the shaped breast part 10. Textile insert 40 is embedded in such a way that it runs in an inclined manner from the outer edge to the inner edge. It is drawn approximately 2 to 3 cm deep into the plastic layer towards cavity 20, whereas it has superficial contact on the outside.

What is claimed is:

1. An elastic plastic breast prosthesis comprising a hollow breast-shaped member simulating the shape of the natural female breast and having a hollow space therein bonded by the inside of said breast-shaped member and the inside wall of a contact surface adapted for contact with the human body when said breast prosthesis is worn, said contact surface having an opening therethrough to the inner space of the breast-shaped member; and at least two substantially vertical reinforcing ribs extending into the inner space from the lateral inner wall surface of the breast-shaped member to reinforce a peripheral area thereof, while forming a free space allowing the breast-shaped member to be inverted over when pressure is exerted thereon and being supported by said inside of said breast-shaped member in the upper portion of said inner space and by said inside wall of said contact surface bounding the lower portion of said inner space in such a way that when the breast-shaped member is inverted over, said ribs roll downwards.

2. A breast prosthesis comprising an elastic plastic, hollow breast-shaped member simulating the shape of the natural female breast, having a hollow inner space therein bounded by the inside of said breast-shaped member and the inside wall of a contact surface adapted for contact with the human body when said breast prosthesis is worn, said contact surface having an outer edge and an opening therethrough to the inner space of the breast-shaped member surrounded by an inner edge; at least two substantially vertical reinforcing ribs extending into the inner space from the lateral inner wall surface of the breast-shaped member to reinforce a peripheral portion of said breast-shaped member, said ribs being arranged in said hollow inner space while forming a free space allowing the breast-shaped member to be inverted over when pressure is exerted thereon and being supported by said inside of said breast-shaped member in the upper hollow space area and by said inside wall of said contact surface bounding the lower hollow space area in such a way that when the breast-shaped member is inverted over, said ribs roll downwards; and a reinforcing insert adjacent to said contact surface, made from a textile fabric, and inclined from the outer edge of said contact surface towards the inner edge of said contact surface and said hollow inner space and partially embedded in said contact surface.

3. A breast prosthesis according to claim 1 or 2 having three equidistant reinforcing ribs.

4. A breast prosthesis comprising an elastic, deformable breast-shaped part having a contact surface adapted for mounting the prosthesis on a patient, said breast-shaped part having a hollow interior bounded by the interior walls of said breast-shaped part and the interior walls of said contact surface and in communication with the exterior of the prosthesis through a central opening in said contact surface, a plurality of flexible web-like ribs in the periphery of said hollow interior connected to the interior wall of said contact surface radially outward from said opening and to the interior peripheral walls of said breast-shaped part.

5. A breast prosthesis as claimed in claim 4 wherein said hollow interior has a toroidal portion coaxial with said central opening and said ribs are entirely contained within said toroidal portion.

6. A breast prosthesis as claimed in claim 4 made of silicone rubber.

7. A breast prosthesis as claimed in claim 6 wherein a textile fabric is embedded in said contact surface.

8. A breast prosthesis as claimed in claim 5 or 6 having two of said ribs, on opposed sides of said central opening, oriented to be substantially vertical when said breast prosthesis is worn.

9. A breast prosthesis as claimed in claim 5 or 6 having three of said ribs equidistantly spaced in said hollow interior.

10. A breast prosthesis as claimed in claim 4 further comprising a textile insert embedded in said contact surface at an incline such that it is deeper in said contact surface toward said hollow interior near said central opening than radially outward therefrom.

* * * * *